United States Patent [19]

Ananthapadmanabhan et al.

[11] Patent Number: 6,045,817
[45] Date of Patent: Apr. 4, 2000

[54] ULTRAMILD ANTIBACTERIAL CLEANING COMPOSITION FOR FREQUENT USE

[75] Inventors: Kavssery Parameswaran Ananthapadmanabhan, Highland Mills; Kam Kuen Chan, New York, both of N.Y.; Dale Albert Grinstead, Cincinnati, Ohio; Carol Kregler Vincent, Wanaque, N.J.; Arnoud Ubald Maria Gengler, Maarssen, Netherlands

[73] Assignee: Diversey Lever, Inc., Plymouth, Mich.

[21] Appl. No.: 09/156,415

[22] Filed: Sep. 18, 1998

Related U.S. Application Data

[63] Continuation-in-part of application No. 08/937,667, Sep. 26, 1997.

[51] Int. Cl.⁷ ..................................................... A01N 25/00
[52] U.S. Cl. ........................ 424/405; 424/400; 424/78.03
[58] Field of Search ..................................... 424/405, 400, 424/78.03

[56] References Cited

U.S. PATENT DOCUMENTS

| | | | |
|---|---|---|---|
| 2,684,924 | 7/1954 | Rose et al. .................................. | 167/30 |
| 2,990,425 | 6/1961 | Senior ....................................... | 260/501 |
| 3,468,898 | 9/1969 | Cutler et al. .............................. | 260/301 |
| 4,022,834 | 5/1977 | Gundersen ........................... | 260/564 B |
| 4,053,636 | 10/1977 | Eustis, III et al. ....................... | 424/326 |
| 4,326,977 | 4/1982 | Schmolka ................................. | 252/106 |
| 4,748,158 | 5/1988 | Biermann et al. ......................... | 514/25 |
| 4,919,837 | 4/1990 | Gluck ....................................... | 252/106 |
| 5,164,107 | 11/1992 | Khan et al. ............................... | 252/106 |

FOREIGN PATENT DOCUMENTS

| | | |
|---|---|---|
| 024 031 | 8/1980 | European Pat. Off. . |
| 2212259 | 3/1972 | Germany . |
| 2627548 | 6/1976 | Germany . |
| 94/05753 | 3/1994 | WIPO . |
| 95/31962 | 11/1995 | WIPO . |

*Primary Examiner*—S. Mark Clardy
*Assistant Examiner*—Kathryne E. Shelborne

[57] ABSTRACT

An antibacterial cleaning composition is described which has about 0.05 to about 1 wt. % of a cationic polymer having a charge density of 0.0025 or higher, about 0.2 to about 5% of a zwitterionic surfactant, about 0.2 to about 5 wt. % of at least one biguanide compound, and optionally a nonionic surfactant and a polymeric biocide compound. The composition has a pH of 7.5 or greater.

14 Claims, No Drawings

ULTRAMILD ANTIBACTERIAL CLEANING COMPOSITION FOR FREQUENT USE

RELATED FIELD

The application is a continuation-in-part of U.S. Ser. No. 08/937,667 filed Sep. 26, 1997.

FIELD OF THE INVENTION

This invention relates to a highly effective antibacterial cleaning composition which is mild enough for frequent use and which contains a selected cationic polymer, a zwitterionic surfactant, at least one cationic antibacterial agent, and optionally a nonionic surfactant in a composition having a pH of 7.5 or greater.

BACKGROUND OF THE INVENTION

Frequent handwashes are an important part of a hygiene program for health care workers and food handlers. It is not unusual for such personnel to wash their hands twenty times a day or more. Many antiseptic products used in the settings are harsh and cause significant irritation upon repeated use. This leads to poor compliance by the personnel with required handwash guidelines. Thus, the present invention provides a highly effective antibacterial cleansing composition which is mild enough for frequent use.

Biguanide compounds, such as chlorhexidine salts, are mild antibacterial agents which have a strong affinity for binding to the skin. However, several formulation issues arise when producing compositions containing chlorhexidine. Since chlorhexidine is a cation it is incompatible with anionic materials and additionally can react with the counterion of some compatible cationic compounds to form a less soluble salt leading to precipitation of the chlorhexidine.

WO 95/31962 (Gojo Industries, Inc.) describes an antibacterial cleansing composition containing a salt of chlorhexidine and at least one nonionic surfactant which does not include any polyoxypropylene/polyoxyethylene copolymers. The composition is also described as containing at least one amphoteric surfactant and quaternary ammonium surfactants may optionally be added.

Biermann et al., (U.S. Pat. No. 4,748,158) relates to the use of alkylpolyglycoside as an agent used to increase the microbiocidal activity of biguanide compounds. The resulting biguanide compositions are useful in the oral health field, particularly in toothpaste and mouthwashes. The compositions may also contain numerous factors including nonionic, cationic, zwitterionic and amphoteric surfactants, as well as thickeners such as hydroxyethylcellulose.

WO 94/05753 owned by Henkel Corp. describes an aqueous disinfectant cleaning composition whose activity is increased by incorporating an effective amount of a compound having the formula (I):

R—O(—G)$_n$     (I)

wherein R is an alkyl group having from about 8 to about 22 carbon atoms, G is a saccharide residue having 5 or 6 carbon atoms; and n is a number from 1 to 10 into an aqueous composition which contains a compound of the formula II:

R$_2$R$_3$R$_4$R$_5$NX     (II)

wherein R$_2$ is a benzyl or C$_{1-14}$ alkyl substituted benzyl group, and each of R$_3$, R$_4$, and R$_5$ is independently an alkyl group having from about 8 to about 22 carbon atoms.

U.S. Pat. No. 4,919,837 issued to Gluck describes antiseptic cleaning compositions containing the salt of chlorhexidine in combination with at least one nonionic surfactant and a carrier wherein the weight ratio of the chlorhexidine salt to the nonionic surfactant is not more than 1:7.

Bectin Dickinson owns U.S. Pat. No. 5,164,107 which describes a surgical scrub containing chlorhexidine and nonylphenoxypoly (ethyleneoxy), ethanol surfactant in combination with other surfactant thickeners, etc. in an aqueous vehicle.

BASF owns U.S. Pat. No. 4,326,977 describing a skin cleaning compositions comprising chlorhexidine and a polyoxyethylene/polyoxybutylene block copolymer wherein the polyoxybutylene portion of the compound has a molecular weight of from 500 to 2000.

Accordingly, an antibacterial composition which is highly effective for killing bacteria and other microorganisms, but which is also mild enough for frequent use in a single day is described.

SUMMARY OF THE INVENTION

It is therefore an object of the present invention to provide a cleansing composition which is highly effective in killing bacteria and other microorganisms and yet is mild enough for frequent use.

It is still another object of the present invention to provide an antibacterial cleaning composition which includes a biguanide, particularly a salt of chlorhexidine, at least one zwitterionic surfactant, a cationic polymer having a charge density of 0.0025 moles per gram or higher, preferably 0.005 moles per gram or higher, and most preferably 0.05 moles per gram or higher and optionally, a nonionic surfactant.

The composition exhibits having a pH of 7.5 or greater. A method of using the inventive composition is also described.

It has been unexpectedly discovered that the addition of the selected cationic polymer significantly increases the antibacterial effect of the biquanidine active in a pH range higher than that thought to be effective for the antibacterial agent. Thus, not only has a highly effective antibacterial composition been discovered, but the composition may be formulated in pH ranges higher than those taught possible in the art to increase the antibacterial range of the composition.

Moreover, the inventive compositions are significantly milder than those of the prior art. They also exhibit a desirable sensory feel, thus promoting frequent hand washing by health care employees and food handlers preventing the spread of harmful bacteria.

PREFERRED EMBODIMENTS OF THE INVENTION

The present invention is directed toward an antibacterial composition which effectively kills bacteria and other microorganisms but is extremely mild on the user's skin even multiwash users in such settings as healthcare and food handling. The compositions of the invention have been found to significantly reduce a number of colony forming units (CFUs) of bacteria such as *P. aeruginosa, E. hirae, S. aureus,* and *E. coli* and at a pH level which increase the effectiveness of the active ingredients of the invention.

The essential ingredients for the antimicrobial cleansing composition having a pH of 7.5 or greater includes at least one biguanide compound, preferably a salt of chlorhexidine, a zwitterionic surfactant such as propionate, and a cationic polymer having charge density higher than 0.0025 moles per gram. In a preferred embodiment, a nonionic surfactant and a polymeric biocide compound are also present.

Cationic Polymer

An effective amount of preferably about 0.05 to about 1 wt. % of a selected cationic polymer is a critical aspect of the invention.

Cationic charge density of the polymer can be defined either as the effective cationic charge per unit length of the polymer chain (linear charge density equals total number of charges on a polymer molecule divided by the average length of the polymer chain) or in terms of number of charges in moles per unit weight of the polymer (total number of cationic charges on a repeat unit of which the polymer is comprised of, divided by the molecular weight of the repeat unit). For the purposes of this application, we have defined the charge density of the polymer molecule in terms of number of charges per unit weight. Thus, the charge density is essentially given by:

Charge density=Total number of charges per repeat unit

Molecular weight of the repeat unit or

Total number of charges per polymer chain

Molecular weight of the polymer

Examples of suitable polymers useful for the invention include polyethyleneimine (-{CH$_2$—CH$_2$—NH—},-) supplied by Rhone-Poulenc under the trademark Lupasol™, having a monomer molecular weight of 43 gms. And one charge per monomer unit, has a charge density of 0.023 moles per gm. (1 divided by 43) under acidic pH conditions; polydimethyl diallyl ammonium chloride (Polyquaternium 6, -(C$_8$H$_{16}$NaCl)$_n$ supplied by Calgon under the trademark Merquat™ with a monomer molecular weight of 163.5 and one charge per monomer has a charge density of 0.0061 moles per gm; Mirapol A-15 (Polyquaternium 2) supplied by Rhone-Poulenc having two quaternary charged groups per monomer unit and a molecular weight of 373 has a charge density of 0.0054 moles per gram. In the case of modified cellulosic type polymers such as Polymer JR (Polyquaternium 10) supplied by Amerchol, the charge density may have to be estimated by polyelectrolyte titration techniques or by estimating the amount of surfactant required to cause all the polymer to precipitate. Charge density of Polymer JR estimated in this manner is around 0.00175 moles per gram.

The molecular weight of the polymer is 300 to 500,000 daltons, preferably 2000 to 250,000, most preferably 5000 to 100,000.

Biguanide Compounds

As examples of the microbiocidal agents which can be used according to the present invention there can be antiseptic biguanide compound such as chlorhexidine (which is the common name for the antiseptic 1, 1'-hexamethylene-bis-[5-(4-chlorophenyl) -biguanide] widely used in the form of its salts (such as the acetate, hydrochloride, and gluconate salts) in the cosmetic and pharmaceutical fields and also in cleaning preparations).

Numerous antimicrobial biguanide compounds which can be used in the present invention are mentioned in the patent literature, including, for examples, European Patent No. 24,031; U.S. Pat. Nos. 2,684,924; 2,990,425; 3,468,898; 4,022,834 and 4,053,636; and German patent Nos. 2,212, 259 and 2,627,548. Additional examples of antimicrobial biguanide compounds, which can be utilized in the present invention include N$^1$-(4-chlorobenzyl)-N$^5$-(2,4-dichlorobenzyl)-biguanide; p-chlorophenyl biguanide; 4-chlorobenzhydryl biguanide; N-3-lauroxypropyl-N$^5$-p-chlorobenzyl biguanide; N$^1$-p-chlorophenyl-N$^5$-lauryl biguanide and the non-toxic addition salts thereof, especially gluconates and acetates.

A salt of chlorhexidine is selected for its antibacterial activity for the active ingredients of the present invention. The salt is present in a range of about 0.2 to 5% by weight, preferably 0.5 to 4.5% by weight, and most preferably 1 to 4% by weight. It is appreciated that for purposes of this invention all percentages recited herein are based on the percent active by way of the composition unless otherwise indicated.

Any salt of chlorhexidine which is soluble in water or another non-alcohol solvent may be used in the composition of the present invention. Such salts include gluconate, acetate, formate, lactate, isethionate, succinamate, glutamate, mono-diglycollate, dimethanesulfonate, di-isobutyrate, glucoheptonate. Preferably, the chlorhexidine salts are gluconate and acetate, the most preferred being chlorhexidine digluconate. Also preferred is the use of salts of polyhexamethylene biguanide compounds in combination with chlorhexidine salts.

Polymeric Biocide Compounds

In a preferred embodiment a polymeric biocide compound is present in the composition in an amount of up to 5 wt. %, preferably 0.005 to 5 wt. %, most preferably 0.05 to 2 wt. %. Suitable compounds include the salts of polyhexamethylene compounds, under the tradename Cosmocil CQ and Vantocil IB, having the following general formula:

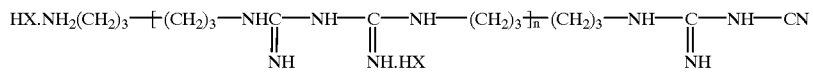

in which HX is the salt-forming acid component, such as HCl, for example, and n is a number having a value of at least 2, and preferably having a value of from about 8 to 12.

Nonionic Surfactant

Nonionic surfactants may optionally be present in the inventive compositions as described below.

Alcohol ethoxylates are suitable for the present composition and preferably have an EO length of 9 to 22, most preferably about 15 to about 21. A preferred example is C$_{13}$-oxoalcohol polyglycol ether (EO=20). This alcohol is available from Huls AG of Marl, Germany, under the trademark Marlipai 013/200. Other alcohols which are suitable for this invention include linear C$_{12}$–C$_{15}$ alcohol ethoxylate a(EO=12), under the tradenames Neodol 25-12 (Shell Chemical Co.) and Rhodasurf LA-12 (Rhone-Poulenc). Still other alcohol ethoxylate which can be used are C$_{12}$–C$_{15}$ alcohol ethoxylate (EO=9), under the tradenames Neodol 25-9 (Shell Chemical Co.) and C$_{14}$–C$_{15}$ alcohol ethoxylate (EO=13), under the tradenames Neodol 43-13 (Shell Chemical Co.).

Another nonionic surfactant suitable for the present invention is alkylpolyglycoside having a formula:

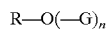

wherein R is an alkyl group having from about 8 to about 22 carbon atoms, G is a saccharide residue having 5 or 6 carbon atoms and n is a number from 1–10.

Alkylpolyglycoside suitable in the invention are described in WO 94/05753 and U.S. Pat. No. 4,748,158, both owned by Henkel and hereby incorporated by reference. Specifically, the alkylpolyglucoside compounds are commercial surfactants and are available, for example, from Henkel Corporation, Hoboken, N.J., under the trademark names APG®, Plantaren™, or Glucopon™ and from Seppic (France) under the trademark Oramix™. Examples of such surfactants include but are not limited to:

1. an alkylpolyglycoside in which the alkyl group contains 8 to 10 carbon atoms,
2. an alkyl polyglycoside in which the alkyl group contains 9 to 11 carbon atoms.
3. Gluopon™ 625—an alkyl polyglycoside in which the alkyl groups contains 12 to 16 carbon atoms,
4. APG™ 300—an alkyl polyglycoside substantially the same as the 325 product above but having a different average degree of polymerization,
5. Glucopon™ 600—an alkylpolyglycoside substantially the same as the 625 product above but having a different average degree of polymerization,
6. Plantaren™ 2000—a $C_{8-16}$ alkyl polyglycoside,
7. Plantaren™ 1300—a $C_{12-16}$ alkyl polyglycoside,
8. Plantaren™ 1200—a $C_{12-16}$ alkyl polyglycoside,
9. Oramix NS10.

Another nonionic surfactant suitable for the present invention is a polymeric surfactant comprised of polyoxyethylene and polyoxypropylene. These block copolymers are sold under the tradename Pluronics.

When nonionics are employed, they are preferably incorporated in amounts ranging from 0 to about 10 wt % active of the entire composition, with the range of 0–2 wt % active being most preferred.

Zwitterionic Surfactant

Useful zwifferionic surfactants for the present invention are well known in the detergent art and are described at length in "Surface Active Agents in Detergents", Vol. 2, by Schwartz, Perry and Birch, Interscience Publishers, Inc. 1959, herein incorporated by reference.

In the preferred embodiments the zwitterionic or amphoteric surface active agents are agents having a propionate or betaine or sultaine structure corresponding a general formula selected from the group consisting of:

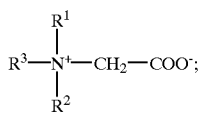

(1)

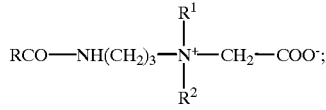

(2)

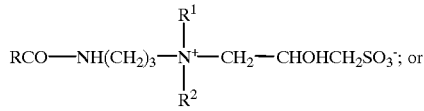

(3)

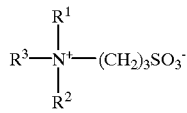

(4)

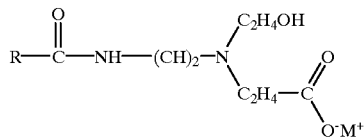

(5)

where $R^1$ and $R^2$ are the same or different and are selected from the group consisting of an alkyl radical having about 1 to 4 carbon atoms and a hydroxyalkyl radical having about 2 to 3 carbon atoms and, preferably, both being methyl groups;

$R^3$ is an alkyl radical having about 8 to 18 carbon atoms; and

R is an alkyl radical having about 7 to 17 carbon atoms; R and its bonded carbonyl group (RCO—) is preferably derived from a $C_{12}$–$C_{18}$ fatty acid. Preferred $C_{12}$–$C_{18}$ fatty acids are lauric acid, myristic acid, stearic acid, tallow acids or coconut fatty acids, Example betainic agent of formula (1) are alkylbetaines where the alkyl group is derived from coconut fatty acids or tallow acids. Suitable alkylbetaines are given the respective means of Coco-betaine and Dihydroxyethyl tallow glycinate in the CTFA Cosmetic Ingredient Dictionary (hereinafter "CTFA Dictionary"), 3rd ed., 1982, published by the Cosmetic, Toiletry and Fragrance Association and in the Cosmetic Bench Reference encyclopedia of cosmetic materials (hereinafter "Bench Reference"), Cosmetics & Toiletries, 1984 edition, August 1984, and its addenda, December. 1984 the disclosures of which are incorporated herein by reference.

Particularly preferred alkylbetaines are the coco-betaines available under the trademark designations Lonzaine 12C from Lonza, Inc., Fairlawn, N.J. and Schercotaine CB from Scher Chemicals, Inc., Clifton. N.J.

An example of a betainic agent of formula (2) is an alkylamidobetaine where the alkyl radical and its bonded carbonyl group (RCO—) are preferably derived from a fatty acid, such as lauric acid, myristic acid, stearic acid, tallow acids or coconut fatty acids. Suitable alkylamidobetaines are given the respective names lauramidopropyl betaine, myristamidopropyl betaine, stearamidopropyl betaine and cocoamidopropylbetaine in the CTFA Dictionary. Particularly preferred alkylamidobetaines are available under the trademark designations Rewoteric AMB13, AMB14, AMB14LS supplied by Witco, and Tegobetaine E supplied by Goldschmidt.

An example of a sultaine of formula (3) is one in which the alkyl radical R and its bonded carbonyl group (RCO—) are preferably derived from a fatty acid such as lauric acid, stearic acid, tallow acids, coconut fatty acids and the like. A particularly preferred sultaine is an alkylamidopropylhydroxy-propylsulfobetaine where the alkyl radical R contains about 7 to about 17 carbon atoms, and where R and its bonded group (RCO—) are preferably derived from coconut fattys. An illustrative sultaine is given the name cocamidopropylhydroxysultaine in the CTFA Dictionary and in the Bench Reference.

Particularly preferred sultaines are available under the trademark Varion CAS from Sherex Chemical Company, Inc., subsidiary of Schering A.G., Dublin, Ohio, and Mirataine CBS from Rhone-Poulenc Inc., Cranbury, N.J.

An example of sultaine agent of formula (4) is an alkylsultaine in which the quaternized nitrogen atom is bonded directly to a carbon atom of an alkyl moiety preferably derived from coconut fatty acids. A suitable alkylsultaine is given the name cocosultaine in the CTFA Dictionary and in the Bench Reference.

An example of a betainic agent of formula (5) is an alkylamphopropionate Suitable alkylamphopropionates are given the respective names cocoamphopropionate, caprylocamphopropionate in the CTFA Dictionary. Particularly preferred alkylamphopropionate is available under the trademark designations Rewoteric AM-KSF40 supplied by Witco.

Preferred zwitterionic surfactants are present in an amount of 0.2 to about 5%, preferably 0.5 to about 3%, most preferably 0.5 to about 2%.

pH Range

It was unexpectedly discovered that not only does the combination of the biguanide compounds with the selected cationic polymers of the invention significantly increase the activity of the antibacterial active but further alters the activity and chemical stability profile of the compounds. In aqueous solutions, chlorhexidine salts in particular generally display a maximum biological activity and chemical stability within a pH range of 5–8. The compositions of the invention exhibit maximum biological activity and stability in a pH range of 7.5 and greater, preferably 7.5 to 10, most preferably 7.5 to 9.

Salt Content

In the preferred embodiments, the final composition should exhibit a relatively low salt content for the stability of the compositions.

Additional Polymers

In the preferred embodiments, additional cationic, non-ionic or zwitterionic polymers may be incorporated into the formulations to provide desirable, tactile and sensory characteristics of the products.

Optional Ingredients

The composition may also include other additives such as thickeners, emollients, quaternary ammonium surfactants, foaming agents, fragrances, coloring agents, preservatives, fungicides, pacifying agents, pearlizing agents, vitamins and the like. For example, the composition may include a polymer viscosifier or thickener such as hydroxyethyl cellulose to make the composition more stable. Samples of other suitable polymer viscosifiers include, but are not necessarily limited to hydroxypropylcellulose, methylcellulose and carboxymethylcellulose. Each additive, when present, is added in amounts up to 0.5% by weight, preferably 0.001 to about 10% by wt., most preferably 0.01 to about 5% by wt.

The balance of the composition is typically water or another non-alcohol solvent so as to provide 100% by weight of a composition.

The antimicrobial cleaning composition of the present invention is generally prepared by dissolving the various ingredients such as the alkylpolyglucoside, the zwitterionic surfactant, the soluble salt of chlorhexidine, and the selected cationic polymer in water with stirring. Any viscosifier has been preferably added and the solution been mixed until it is completely hydrated. The pH is checked and adjusted with acid or base, if necessary. Any acid or base compatible with the components of the formulation can be used. Preferred acids include citric acid, phosphoric acid, gluconic acid, lactic acid, acetic acid, and glycolic acid with citric acid and phosphoric acid being most preferred. Preferred bases include sodium hydroxide, potassium hydroxide, and triethanolamine with sodium hydroxide being the most preferred. This process can be employed with or without the application of heat to enhance the solution.

Example 1

The antibacterial activities were determined in the CEN test as follows:

Antibacterial Test Procedure (Dilution-Neutralization Method)

The test is performed against four strains of bacteria: *Staphylococcus aureus* ATCC 6538, *Enterococcus hirae* ATCC 10541, *Escherichia coli* (K 12) NCTC 10538 or ATCC strain (10536) and *Pseudomonas aeruginosa* ATCC 15442. The neutralizer used was Butterfield's Phosphate Buffer containing 20X neutralizers (10% Tween 80 and 1.4% lecithin).

The bacterial test suspensions were prepared by transferring loopfuls of the cells from the slants into 9 ml of tryptone sodium chloride diluent in a flask containing 5 g of 4 mm glass beads. The flasks were vortexed for 3 minutes. The number of cells in the suspension was adjusted to $1\times10^8$ to $3\times10^8$ Colony Forming Units (CFU)/ml using McFarland standards. The suspensions were used within two hours. The suspensions were diluted to $10^{-6}$ and $10^{-7}$ using the tryptone sodium chloride diluent; 1 ml aliquots were pour-plated in duplicate in TSA to determine the actual CFU/ml.

Products were prepared as 55% w/w solutions in hard water. The final water hardness in the sample tubes is lower than 300 mg/kg of $CaCO_3$.

Nine ml of the product dilutions were added to sterile test tubes. One ml of the bacterial suspension was added to the tube and the sample was mixed. The activity of the product was determined for a contact time of 1 minute ±5 seconds or 30 seconds ±5 seconds. At the end of the contact time, one ml of the test mixture was placed in a test tube containing 8 ml of neutralizer and 1 ml of water and mixed. After the neutralization time of 1 minute ±5 seconds, the sample was diluted to $10^{-4}$ in tryptone sodium chloride diluent. Duplicate 1 ml aliquots of the $10^{-1}$ to $10^{-4}$ dilutions were pour-plated using TSA. The procedure was repeated for each test organism and product.

All plates, including the organism control count plates, were incubated for 48 hours at 32° C. The number of colonies on the plates were counted using a Quebec colony counter and the number of CFU/ml in the test solution was calculated.

Hygienic handwash products which demonstrate a reduction in viable counts from $1-3\times10^7$ CFU/ml to no more than $3\times10^4$ CFU/ml within the contact time are deemed to have passed the test. This corresponds to a 3 $\log_{10}$ reduction.

Example 2

Effect of pH on AB Activity

To compare the activity of samples of different pH, base formulations were prepared using 2% Rewoteric AM KSF 40, 1% Marlipal 013/200, 0.1% Cosmocil CQ, 10% Glycerin, 0.8% Natrasol 250 H, 0.25% Lupasol P. The chlorhexidine concentration and pH were varied as follows:

Effect of PH on AB Activity
To compare the activity of samples of different pH, base formulations were prepared using 2% Rewoteric AM KSF 40, 1% Marlipal 013/200, 0.1% Cosmocil CQ, 10% Glycerin, 0.8% Natrasol 250H, 0.25% Lupasol P. The chlorhexidine concentration and pH were varied as follows:

| Sample | % Chlorhexidine | pH | Organism | Reduction Log10 CFU/ml |
|---|---|---|---|---|
| A | 2.5 | 8.0 | E. hirae | 2.99 |
|   |     |     | P. aeruginosa | >6.06 |
| B | 2.5 | 7.5 | E. hirae | >2.98 |
|   |     |     | P. aeruginosa | 4.83 |
| C | 3.0 | 8.0 | E. hirae | >6.05 |
|   |     |     | P. aeruginosa | >6.06 |
| D | 3.0 | 7.5 | E. hirae | 3.96 |
|   |     |     | P. aeruginosa | >6.06 |

Example 3

Effect of Polymeric Biocide (Cosmocil CQ)
To compare the activity of samples with and without Cosmocil CQ, base formulations were prepared using 2% Rewoteric AM KSF 40, 1% Marlipal 013/200, 10% Glycerin, 0.8% Natrasol 250H, 0.25% Lupasol P. The chlorhexidine and Cosmocil CQ concentration were varied as follows:

| Sample | % Chlorhexidine | % Cosmocil CQ | Organism | Reduction Log10 CFU/ml |
|---|---|---|---|---|
| E | 2.5 | 0 | E. hirae | 4.48 |
|   |     |   | P. aeruginosa | 2.48 |
| F | 2.5 | 0.1 | E. hirae | 2.99 |
|   |     |     | P. aeruginosa | >6.06 |
| G | 3.5 | 0 | E. hirae | >6.05 |
|   |     |   | P. aeruginosa | 4.19 |
| H | 3.5 | 0.1 | E. hirae | >6.05 |
|   |     |     | P. aeruginosa | >6.06 |

Example 4

Effect of Cationic Polymer (Lupasol P)
To compare the activity of samples with and without cationic polymer, base formulations were prepared using 2% Rewoteric AM KSF 40, 1% Marlipal 013/200, 2.5% Chlorhexidine, 10% Glycerin, 0.1% Vantocil IB, 0.8% Natrasol 250H. The Lupasol P concentration were varied as follows:

| Sample | % Chlorhexidine | % Lupasol P | Organism | Reduction Log10 CFU/ml |
|---|---|---|---|---|
| I | 2.5 | 0.25 | S. aureus | >6.00 |
|   |     |      | E. hirae | >5.94 |
|   |     |      | E. coli | >5.91 |
|   |     |      | P. aeruginosa | >6.06 |
| J | 2.5 | 0 | S. aureus | >6.00 |
|   |     |   | E. hirae | >5.94 |
|   |     |   | E. coli | 2.82 |
|   |     |   | P. aeruginosa | >5.91 |

We claim:

1. An antibacterial cleaning composition comprising
   a) about 0.05 to about 1 wt. % of a cationic polymer having a charge density of 0.0025 or higher;
   b) about 0.2 to about 5% of a zwitterionic surfactant;
   c) about 0.2 to about 5 wt. % of at least one biguanide compound;
   d) 0 to about 10 wt. % of a nonionic surfactant; and
   e) 0 to 5 wt. % of a polymeric biocide compound,
   the composition having a pH of 7.5 or greater.

2. An antibacterial cleaning composition according to claim 1 wherein the cationic polymer has a molecular weight of 300 to 500,000 daltons.

3. An antibacterial cleaning composition according to claim 2 wherein the cationic polymer is selected from the group consisting of polyethyleneimine, polydimethyl diallyl ammonium chloride, polyquaternium 2, a modified cellulosic polymer and mixtures thereof.

4. An antibacterial cleaning composition according to claim 1 wherein the biguanide compound is a salt of chlorhexidine selected from the group consisting of gluconate, acetate, formate, lactate, isethionate and succinamate.

5. An antibacterial cleaning composition according to claim 1 wherein the zwitterionic surfactant is a compound having a propionate, betaine or sultaine structure.

6. An antibacterial cleaning composition according to claim 1 wherein the nonionic is present in an amount of about 0.2 to about 10 wt. %.

7. An antibacterial cleaning composition according to claim 6 wherein the nonionic surfactant is an alkylpolyglucoside having a formula:

$$R-O(-G)_n$$

wherein R is an alkyl group having from about 8 to abut 22 carbon atoms and n is a number from 1–10.

8. An antibacterial cleaning composition according to claim 1 wherein the polymeric biocide compound is a salt of a polyhexamethylene compound having a formula:

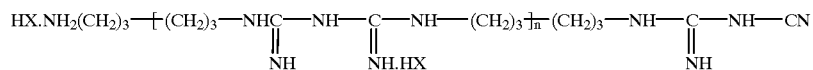

wherein HX is a salt forming acid component and n is 2 to 12.

9. A method of cleaning a surface with an antibacterial cleansing composition comprising the following steps:

a) selecting an antibacterial cleaning composition comprising:
   i) about 0.05 to about 1 wt. % of a cationic polymer having a charge density of 0.0025 or higher,
   ii) about 0.2 to about 5 wt. % of a zwitterionic surfactant,
   iii) about 0.2 to about 5 wt. % of at least one biguanide compound,
   iv) 0 to about 10 wt. % of a nonionic surfactant, and
   v) 0 to 5 wt. % of a polymeric biocide compound; and
b) cleansing a surface with the composition.

10. A method according to claim 9 wherein the cationic polymer has a molecular weight of 300 to 500,000 daltons.

11. A method according to claim 9 wherein the cationic polymer is selected from the group consisting of polyethyleneimine, polydimethyl diallyl ammonium chloride, polyquaternium 2, a modified cellulosic polymer and mixtures thereof.

12. A method according to claim 9 wherein the biguanide compound is a salt of chlorhexidine selected from the group consisting of gluconate, acetate, formate, lactate, isethionate and succinamate.

13. A method according to claim 9 wherein the zwitterionic surfactant is a compound having a propionate, betaine or sultaine structure.

14. A method according to claim 9 wherein the surface is a skin surface.

* * * * *